US005741441A

United States Patent [19]
Watts et al.

[11] Patent Number: 5,741,441
[45] Date of Patent: Apr. 21, 1998

[54] NON-LIQUID SCATTER STANDARD

[75] Inventors: Richard P. Watts, Diamond Bar; Jack D. McNeal, Long Beach, both of Calif.

[73] Assignee: Beckman Instruments, Inc., Fullerton, Calif.

[21] Appl. No.: 675,587

[22] Filed: Jul. 3, 1996

[51] Int. Cl.$^6$ ............................. G01N 21/00; G01J 4/00; G02B 5/00; C08J 5/00; C08K 13/00
[52] U.S. Cl. ............... 252/408.1; 252/582; 356/243; 524/430; 524/500; 524/588; 528/15; 528/22
[58] Field of Search ............... 252/408.1, 582; 356/243; 528/15, 22; 524/500, 588, 430

[56] References Cited

U.S. PATENT DOCUMENTS

| Re. 33,289 | 8/1990 | Modic | 428/145 |
|---|---|---|---|
| 4,059,357 | 11/1977 | Klein | 356/243 |
| 4,322,164 | 3/1982 | Shaw et al. | 356/243 |
| 4,322,517 | 3/1982 | Deubzer et al. | 528/14 |
| 4,340,709 | 7/1982 | Jeram et al. | 528/15 |
| 4,347,346 | 8/1982 | Eckberg | 528/15 |
| 4,439,347 | 3/1984 | Sun et al. | 252/408.1 |
| 4,461,718 | 7/1984 | Kaye et al. | 252/408.1 |
| 4,490,500 | 12/1984 | Smith | 524/378 |
| 4,492,786 | 1/1985 | Evans et al. | 524/865 |
| 4,587,137 | 5/1986 | Eckberg | 427/54.1 |
| 4,681,963 | 7/1987 | Lewis | 556/453 |
| 4,689,384 | 8/1987 | Kondow et al. | 528/15 |
| 4,871,782 | 10/1989 | Modic et al. | 521/88 |
| 4,954,533 | 9/1990 | Modic et al. | 521/82 |
| 5,025,073 | 6/1991 | Lewis et al. | 528/15 |
| 5,034,061 | 7/1991 | Maguire et al. | 106/287.14 |
| 5,123,738 | 6/1992 | Yonemura | 356/243 |

FOREIGN PATENT DOCUMENTS

0374034 A2  6/1990  European Pat. Off.

OTHER PUBLICATIONS

PCT International Search Report (1997).
GE Silicones, RTV615, RTV655—High Strength Transparent Silicone Rubber Compound, 1991.

*Primary Examiner*—Sharon Gibson
*Assistant Examiner*—Deanna Baxam
*Attorney, Agent, or Firm*—William H. May; G. T. Hampson; Margaret A. Kivinski

[57] ABSTRACT

A non-liquid scatter standard for use in nephelometry and turbidimetry systems which comprises a clear silicon rubber gel in which an effective light scattering amount of inorganic particles are suspended. The particles have an index of refraction greater than that of the silicon rubber gel.

8 Claims, No Drawings

NON-LIQUID SCATTER STANDARD

BACKGROUND OF THE INVENTION

Many materials have the ability to transmit or absorb certain wavelengths of light. In the fields of compositional analysis, this phenomenon has been put to good use. For example, if white light containing the full spectrum of light wavelengths is passed through a material sample, the light emerging from the sample will be modified according to the absorptive qualities of the material as to each of the wavelengths of the light. Such "filtered" light then can be analyzed, and by comparison to known standards, the composition of the material or presence of specific components can be determined. The need for light scatter or absorption standards has resulted in various approaches to the formulation of standards.

Klein U.S. Pat. No. 4,059,357 discloses a densitometer standard having a series of bands of different predetermined optical density imposed on an optically transparent substrate. The substrate is homogeneous transparent material such as glass, plastic film, etc. The bands are photographically developed emulsions or chemically etched films such as chromium present as a thin film on the surface of the substrate.

Kaye et al. U.S. Pat. No. 4,461,718 describes a wavelength calibration solution comprising an acidic aqueous medium containing from neodymium and samarium, wherein the neodymium is present as a neodymium ionized constituent and the samarium is present as a samarium ionized constituent used for checking the wavelength accuracy of spectrometers or spectrophotometers.

Sun et al. U.S. Pat. No. 4,439,347 also discloses an acidic aqueous solution for checking the photometric accuracy of a spectrometer or spectrophotometer which comprises cobalt ammonium sulfate and sulfuric acid. The aqueous solution is particularly intended for checking the linearity of response of a spectrometer or spectrophotometer.

Smith U.S. Pat. No. 4,490,500 relates to a two component curable silicon composition for encapsulating photovoltaic cells and potting automotive electrical components. The composition is either free of fillers or contains extending or pigmenting fillers in amounts which render the composition opaque to light. There is no reference to the use of small, light scattering amounts of any particles or to a preference for particles having an index of refraction greater than the cured silicon.

In nephelometry one example of a light scatter standard is used on the ARRAY® Protein System, produced by Beckman Instruments, Inc., Fullerton, Calif. This system uses a liquid scatter standard that consists of a detergent emulsion. The emulsion is degassed and placed in a cylindrical glass ampoule which is then flame sealed to prevent air entry. This ampoule is placed into the ARRAY light path and the signal measured. More recent systems use plastic or glass cuvettes of approximately rectangular shape which make it difficult to prevent air bubble entrapment and to get reliable sealing when using a liquid standard. In addition these emulsions are not particularly robust and require care on the part of the operator not to shake or foam the emulsion during use. Attempts to make solid scatter standards with long usable life, by the encapsulation of fluorescent dyes in polymerized solids such as methacrylate, polyester, or epoxy have been problematic. First, the fluorescent dyes bleach significantly both in room light over several months and under the intense light of the optical systems. Second, the use of highly polarized visible laser diodes as an optical source reveal intense polarization effects likely resulting from the internal stresses inherent in the solid plastics after polymerization.

This invention relates to a non-liquid scatter standard, particularly adapted for use on nephelometry and turbidimetry systems, which overcomes these problems.

SUMMARY OF THE INVENTION

The invention comprehends a non-liquid scatter standard for use in nephelometry and turbidimetry systems which comprises a clear silicon rubber gel in which an effective light scattering amount of light scattering inorganic particles are suspended. The inorganic particles have an index of refraction greater than that of the silicon rubber gel.

The non-liquid scatter standard of this invention comprises a normal cuvette configured for the specific nephelometry or turbidimetry system filled with a clear silicon rubber gel in which effective, light scattering amounts of inorganic particles are suspended.

The silicone rubber gels of this invention have an index of refraction of about 1.3 to about 1.5. The inorganic particles must have a greater index of refraction than the silicon gel, and normally have an index of refraction on the order of 1.7 or more, preferably from about 1.8 to about 3.0 or higher. Particles of zinc, antimony, and titanium oxides are preferred. Other metal oxides having high index of refraction can also be used. In the preferred embodiment, particles of $TiO_2$ (titanium dioxide) are used.

The weight to volume ratio of the inorganic particles to the clear silicon rubber gel is usually on the order of about 0.0001 mg/ml to about 0.010 mg/ml.

The significance of the invention is that the polymerized silicone rubber forms a gel structure which does not exhibit intense polarization effects found in other polymerized solids. This lack of polarization effects is likely due to the random and pliable structure of the gel which does not exhibit internal stresses. The use of solid inorganic particles such as titanium dioxide provides a light scattering source and eliminates the problem with the bleaching of organic dyes. The silicone rubber gels do not evaporate so the need to seal the cuvette is also eliminated.

The advantages of this non-liquid scatter standard are, in summary: 1) does not exhibit intense polarization effects so the use of highly polarized sources such as laser diodes is made possible; 2) uses highly stable inorganic pigments, eliminating the possibility of fading or photobleaching; 3) can be made in cuvettes of any shape or form; 4) does not evaporate, eliminating the need for sealing the cuvette; and 5) can not be spilled, or foamed like a liquid.

The silicone rubber gel can be used to fill any normal container. This makes it possible to use this invention in any Nephelometry or Turbidimetry system in the future.

DESCRIPTION OF PREFERRED EMBODIMENTS

The clear silicon rubber gels used in the practice of this invention are a self-bonding, solventless, room temperature vulcanizable silicone rubber compositions preferably formed from two components.

Component A

A mixture, sometimes referred to as "monomer", comprising (1) 83 to 98.6 parts by weight of a silanol endstopped diorganopolysiloxane polymer having a viscosity varying from 100 to 4000 centipoise at 25° C., wherein the organo groups are monovalent hydrocarbon radicals such as methyl, vinyl or phenyl, and (2) 1.4 to 17 parts by weight of resinous copolymer comprising $R_3SiO_{0.5}$ units and $SiO_2$ units, wherein R is a monovalent hydrocarbon radical and wherein said copolymer has from 0.5 to 1 $R_3SiO_{0.5}$ unit per $SiO_2$ unit.

Component B

A reacted catalyst mixture comprising;

(1) 10 to 50 parts by weight of an alkyl silicate of the formula

$(R^1)_mSi(OR^2)_{4-m}$ and partial hydrolysis products thereof, wherein $R^1$ and $R^2$ are monovalent hydrocarbon radicals, such as methyl, vinyl or phenyl where m is 0 or 1, the preferred alkyl silicate being tetraethyl orthosilicate, and which is pre-reacted with (2) an effective catalytic amount, on the order of at least 10 to 20 parts by weight of, a tin salt of a carboxylic acid, such as dibutyl tin dilaurate, dibutyl tin dioctoate, or dibutyl tin neodecanoate, (3) 10 to 30 parts by weight of a self-bonding additive having the formula

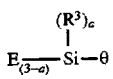

$$E_{(3-a)}\!\!-\!\!\underset{\underset{(R^3)_a}{|}}{Si}\!\!-\!\!\theta$$

wherein $R^3$ is a monovalent hydrocarbon radical, E is a hydrolyzable group selected from the group consisting of alkoxy, phenoxy, amino and diakylamino and θ is a nitrogen functional radical which is reacted with saturated, unsaturated or aromatic hydrocarbon residues which in addition to nitrogen functionality may be functionalized by a radical selected from the group consisting of amino, cyano, thio, oxo and ester, and combinations thereof, and a is a number varying from 0 to 2; and (4) 10 to 50 parts by weight vinyl terminated linear diorganopolysiloxane fluid in a viscosity varying from 100 to 50,000 centipoise at 25° C., wherein the organo groups are monovalent hydrocarbon radicals. Preferably, the vinyl terminated diorganopolysiloxane fluid is a vinyl terminated dimethylpolysiloxane having a viscosity from 100 to 10,000 centipoise at 25° C.

The preferred silanol end-stopped polymer in Component A has the formula

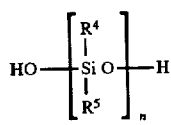

$$HO\!-\!\!\left[\begin{array}{c}R^4\\|\\Si\,O\\|\\R^5\end{array}\right]_n\!\!-\!H$$

wherein $R^4$ and $R^5$ are monovalent hydrocarbon radicals, preferably methyl, and n varies so that the polymer has the viscosity stated above.

In Component A, the preferred resinous copolymer is composed of $(CH_3)_3SiO_{0.5}$ units and $SiO_2$ units wherein the ratio of the monofunctional units to the tetrafunctional units is from 0.5 to 1 to 1 to 1.

In Component B, the preferred self bonding additive is gamma-aminopropyl triethocysilane.

The ratio of Component A to Component B on a weight basis is normally from about 100 to 1 to about 100 to 20.

These two component, silicon gel-forming systems are further described in U.S. Pat. No. 4,490,500.

RTV615 silicone rubber is a transparent liquid which cures with the addition of a catalytic component at room temperature to high strength silicone rubber. These two-component products are supplied by General Electric Silicones in matched kits and are intended for use at a convenient 10:1 ratio by weight. Both components of RTV615 are initially clear and colorless, and are easily pourable liquids with nominal viscosities of between 3000 and 7000 cps.

TABLE 1

UNCURED PROPERTIES

|  | Component A RTV615A | Component B RTV615B |
|---|---|---|
| Color | Clear Colorless | Clear Colorless |
| Consistency | Easily Pourable | Easily Pourable |
| Viscosity, cps | 4300 | — |
| Specific Gravity | 1.02 | — |

TABLE 2

UNCURED PROPERTIES WITH CURING AGENT ADDED

|  | RTV615 |
|---|---|
| Color | Clear, Colorless |
| Consistency | Easily Pourable |
| Viscosity, cPs | 4000 |
| Work Time @ 25 C. (77 F.), hrs | 4 |

TABLE 3

CURED PROPERTIES (Cured 1 hr. @ 100 C./212 F.)

|  | RVT615 |
|---|---|
| Mechanical |  |
| Hardness, Shore A Durometer | 44 |
| Tensile Strength, kg/cm²-(psi) | 65 (920) |
| Elongation, % | 160 |
| Shrinkage, % | 02 |
| Refractive Index | 1.406 |

The preferred inorganic particles are as follows:

TABLE 4

| PARTICLE | INDEX OF REFRACTION |
|---|---|
| Titanium Dioxide | 2.58–2.74 |
| Antimony Trioxide | 2.00–2.08 |
| Zinc Dioxide | 2.00–2.02 |

EXAMPLE 1

PREPARATION OF WORKING SOLUTION OF TITANIUM DIOXIDE ($TiO_2$)

Weigh out 0.015 grams of $TiO_2$ particles on folded weigh paper. Transfer quantitatively all $TiO_2$ to a small area on a glass plate. With a 1 ml disposable syringe, transfer 1 ml of RTV-615/component A to the area of $TiO_2$ on the glass plate. Using a glass flat ended pestle in a rapid circular motion, "grind" the $TiO_2$ and the Component A together until a smooth uniform mixture of particles is achieved. With a small spatula or rubber policeman, scrape the mixture into a 12 mm×75 mm disposable tube. Allow approximately 15 minutes for the mixture to run to the bottom of the tube. ($TiO_2$-0.015 gm/ml). Fill a 10 ml graduated disposable culture tube to the 10 ml mark with Component A. With a 10–100 μl positive displacement pipet, carefully transfer 100 μl of the particle mixture prepared above to the 10 ml tube of Component A. ($TiO_2$-0.00015 gm/ml). With the glass rod, carefully and homogeneously mix the 10 mls of Component A with the particle mixture. Approximately 15 minutes of mixing by hand is sufficient for homogeneity. Place the 10 ml mixture in the centrifuge and spin at 1000 RPM (200G) for approximately 5 minutes to remove bubbles from the mixture. Cap the tube and mark as "Working Solution". ($TiO_2$=0.00015 g/ml).

PREPARATION OF REFERENCE CUVETS

Remove 500 cuvets from bags, apply serializing label to cuvet, and remove dust/particles by blowing off with filtered compressed air. Cuvets are conveniently placed into test tubes held in test tube racks. The racks and cuvets should remain covered until filling to prevent dust entry. Measure 225 ml of RTV-615A (Component A) into a 500 ml glass container. Pipet 2.5 ml of the working solution prepared above into the 500 ml glass container. (Component B) Pipet 22.5 ml of the catalyst RTV-615/B into the 500 ml glass container using a 10 ml disposable syringe. Using the glass stir rod, mix thoroughly by hand for approximately 15 minutes. Working time for the catalyzed silastic is approximately 4 hours at room temperature. After mixing, place the 500 ml container into a centrifuge and spin at 100G for 5 minutes then place into a vacuum desiccator and apply vacuum of approximately 25 in Hg for approximately 30 minutes to remove bubbles. Using a 10 ml disposable syringe, transfer approximately 0.4–0.5 ml of the degassed mixture to each cuvet. After filling, place the filled cuvets into a centrifuge and spin at approximately 1000×G to remove bubbles. Remove the cuvets from the centrifuge and place in 37° C. oven for approximately 14 hours to cure. The weights of $TiO_2$ and volumes of silicon rubber are preferably at a final concentration of 0.0000015 gm/ml. (0.0015 mg/ml).

TESTING OF REFERENCE CUVETS

The IMMAGE reference cuvet test reaction wheel is placed on an IMMAGE instrument. The Immage instrument is described in concurrently filed U.S. patent application Ser. No. 08/674,781. A "Gold Plated Standard" reference cuvet kept and used repeatedly as a standard is placed on the wheel for purpose of comparison, and the remaining cuvet locations are filled with reference cuvets containing the $TiO_2$ and the clear silicon rubber gel described above. The cuvets are read by the IMMAGE instrument for 10 spins using both nephelometric and turbidimetric optics. All reference cuvets are read 5 times in the nephelometric mode first and the turbidimetric mode second and the average values for the MEAN result and data Quality Value (i.e. Max reading-Min reading) are recorded for each cuvet in each mode. The cuvets being tested are then removed and new cuvets to test placed on the wheel.

The results indicated that the optical properties of the reference cuvets were equivalent to the "gold standard" cuvet.

EXAMPLE 2

Add 2.40 mg antimony trioxide powder to 2 ml RTV-615A monomer+1 ml toluene. Sonication for 10 minutes produced a homogeneous mixture. Various samples containing 2 ml to 50 ml of this working solution plus 1 ml was combined with of RTV-615A plus 0.1 ml of RTV-615B were made. The samples were poured into IMMAGE reaction cuvets. (approximately 0.001 mg/ml to 0.04 mg/ml) The cuvets were placed into a vacuum desiccator at 25" Hg for 30 minutes to remove bubbles, and then placed at 37° C. overnight to cure. Each of the cuvets was read on an IMMAGE instrument 10 times and averaged on both the nephelometric and turbidimetric optical channels.

The results indicated that the optical properties were similar to the "gold plated standard" used in the preceding example for comparison.

Having fully described the invention, it is intended that it be limited only by the lawful scope of the appended claims.

We claim:

1. A non-liquid scatter standard for use in nephelometry and turbidimetry systems which comprises a clear silicon rubber gel having an index of refraction of about 1.3 to about 1.5 in which an effective light scattering amount of inorganic particles are suspended, said inorganic particles having an index of refraction greater than that of said silicon rubber gel, and wherein the weight to volume ratio of the inorganic particles to the clear silicon rubber is about 0.0001 mg/ml to about 0.01 mg/ml.

2. The scatter standard of claim 1 wherein the silicon rubber gel is the result of the mixing and curing of two reactive components.

3. The scatter standard of claim 2 wherein one of the components has the composition comprising:

(1) 83 to 98.6 parts by weight of a silanol endstopped diorganopolysiloxane polymer, wherein the organo groups are monovalent hydrocarbon radicals, and (2) 1.4 to 17 parts by weight of resinous copolymer comprising $R_3SiO_{0.5}$ units and $SiO_2$ units, wherein R is a monovalent hydrocarbon radical and wherein said copolymer has from about 0.5 to about 1 $R_3SiO_{0.5}$ unit per $SiO_2$ unit.

4. The scatter standard of claim 2 wherein one of the components has the composition comprising:

(1) 10 to 50 parts by weight of an alkyl silicate of the formula

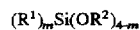

$(R^1)_m Si(OR^2)_{4-m}$ and partial hydrolysis products thereof, wherein $R^1$ and $R^2$ are monovalent hydrocarbon radicals, m is 0 or 1; and which is pre-reacted with (2) an effective catalytic amount of a curing catalyst, (3) 10 to 30 parts by weight of a self-bonding additive having the formula

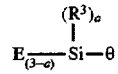

wherein $R^3$ is a monovalent hydrocarbon radical, E is a hydrolyzable group selected from the group consisting of alkoxy, phenoxy, amino and dialkylamino, and θ is a nitrogen functional radical which is reacted with unsaturated or aromatic hydrocarbon residue, which in addition to nitrogen functionality may be functionalized by a radical selected from the group consisting of amino, cyano, thio, oxo and ester, and combinations thereof, and a is a number varying from 0 to 2, and (4) 10 to 40 parts by weight vinyl terminated linear diorganopolysiloxane fluid in a viscosity varying from 100 to 50,000 centipoise at 25° C., wherein the organo groups are monovalent hydrocarbon radicals.

5. The scatter standard of claim 1 wherein the inorganic particles have an index of refraction from about 1.7 to about 3.0.

6. The scatter standard of claim 1 wherein the inorganic particles are titanium dioxide.

7. The scatter standard of claim 1 wherein the inorganic particles are antimony trioxide.

8. The scatter standard of claim 1 wherein the inorganic particles are zinc oxide.

* * * * *